(12) United States Patent
Williams

(10) Patent No.: US 9,833,053 B1
(45) Date of Patent: Dec. 5, 2017

(54) PEDICURE DEVICE WITH TELESCOPING PUMICE STONE

(71) Applicant: Gloria Williams, West Melbourne, FL (US)

(72) Inventor: Gloria Williams, West Melbourne, FL (US)

( * ) Notice: Subject to any disclaimer, the term of this patent is extended or adjusted under 35 U.S.C. 154(b) by 128 days.

(21) Appl. No.: 14/804,700

(22) Filed: Jul. 21, 2015

Related U.S. Application Data

(60) Provisional application No. 62/035,490, filed on Aug. 10, 2014.

(51) Int. Cl.
*A45D 29/05* (2006.01)
*A61B 17/54* (2006.01)

(52) U.S. Cl.
CPC .............. *A45D 29/05* (2013.01); *A61B 17/54* (2013.01); *A45D 2200/1054* (2013.01)

(58) Field of Classification Search
CPC . A45D 29/05; A45D 29/14; A45D 2200/1054
USPC .............................................. 132/76.4, 75.6
See application file for complete search history.

(56) References Cited

U.S. PATENT DOCUMENTS

| | | | | |
|---|---|---|---|---|
| 3,468,079 A * | 9/1969 | Kaufman | ................ | A61B 17/54 407/29.13 |
| 4,213,471 A * | 7/1980 | Burian | .................... | B24B 23/02 132/73.6 |
| 4,683,897 A * | 8/1987 | McBride | ................ | A61B 17/54 132/73 |
| 5,819,757 A * | 10/1998 | Baekkelund | ........... | A45D 29/05 132/73.6 |
| 6,050,270 A * | 4/2000 | Tyshenko, Jr. | ......... | A45D 29/14 132/73.6 |
| 6,865,812 B1 * | 3/2005 | Martin, Jr. | .............. | A45D 29/18 30/27 |
| 7,331,077 B1 * | 2/2008 | Henry | ................... | A46B 5/0033 15/23 |
| 8,226,662 B2 * | 7/2012 | Song | ...................... | A61B 17/54 132/76.4 |
| 9,370,282 B1 * | 6/2016 | Petersen | ................ | A47K 7/028 |
| 2004/0074033 A1 * | 4/2004 | Steinberg | ............ | G06F 13/4068 15/144.4 |
| 2006/0260629 A1 * | 11/2006 | Chern | .................... | A45D 29/05 132/73.6 |
| 2007/0056129 A1 * | 3/2007 | Bohannon | ............ | A46B 5/0095 15/111 |
| 2007/0101522 A1 * | 5/2007 | Alfano | .................. | A46B 13/008 15/22.1 |
| 2009/0301507 A1 * | 12/2009 | Tes | ......................... | A61B 17/54 132/73.6 |
| 2011/0226268 A1 * | 9/2011 | Filonczuk | .............. | A45D 29/05 132/73.6 |

(Continued)

*Primary Examiner* — Tatiana Nobrega

(57) ABSTRACT

The pedicure device with telescoping pumice stone is a device that is adapted for use with pumice stones. The pedicure device with telescoping pumice stone is a telescopic wand that is used to extend the reach of the user when using a pumice stone. The end of the telescopic wand is fitted with an electric motor that is used to rotate the pumice stone while in use. The pumice stone is replaceable, allowing for the user to replace consumed stones or to change the grade or grit of the pumice stone being used. The pedicure device with telescoping pumice stone comprises a handle, a telescopic wand, a motor cap, and a stone cap.

1 Claim, 6 Drawing Sheets

(56) References Cited

U.S. PATENT DOCUMENTS

| | | | | |
|---|---|---|---|---|
| 2014/0096796 A1* | 4/2014 | Frum | ............... | A47L 11/1625 134/6 |
| 2014/0148823 A1* | 5/2014 | Fitzsimons | ............ | A61B 17/54 606/131 |
| 2014/0330289 A1* | 11/2014 | Revivo | ............... | A61B 17/54 606/131 |
| 2015/0150353 A1* | 6/2015 | Yiu | ............... | A45D 29/05 132/75.6 |
| 2015/0165179 A1* | 6/2015 | Grez | ............... | A61M 35/003 604/310 |

* cited by examiner

US 9,833,053 B1

PEDICURE DEVICE WITH TELESCOPING PUMICE STONE

CROSS REFERENCES TO RELATED APPLICATIONS

This non-provisional patent application claims priority to provisional patent application 62/035,490 that was filed on Aug. 10, 2014.

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of pedicure implements, more specifically, a rotating wand adapted to work with a pumice stone.

SUMMARY OF INVENTION

The pedicure device with telescoping pumice stone is a device that is adapted for use with pumice stones. The pedicure device with telescoping pumice stone is a telescopic wand that is used to extend the reach of the user when using a pumice stone. The end of the telescopic wand is fitted with an electric motor that is used to rotate the pumice stone while in use. The pumice stone is replaceable, allowing for the user to replace consumed stones or to change the grade or grit of the pumice stone being used.

These together with additional objects, features and advantages of the pedicure device with telescoping pumice stone will be readily apparent to those of ordinary skill in the art upon reading the following detailed description of the presently preferred, but nonetheless illustrative, embodiments when taken in conjunction with the accompanying drawings.

In this respect, before explaining the current embodiments of the pedicure device with telescoping pumice stone in detail, it is to be understood that the pedicure device with telescoping pumice stone is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the pedicure device with telescoping pumice stone.

It is therefore important that the claims be regarded as including such equivalent construction insofar as they do not depart from the spirit and scope of the pedicure device with telescoping pumice stone. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

Figure 1:
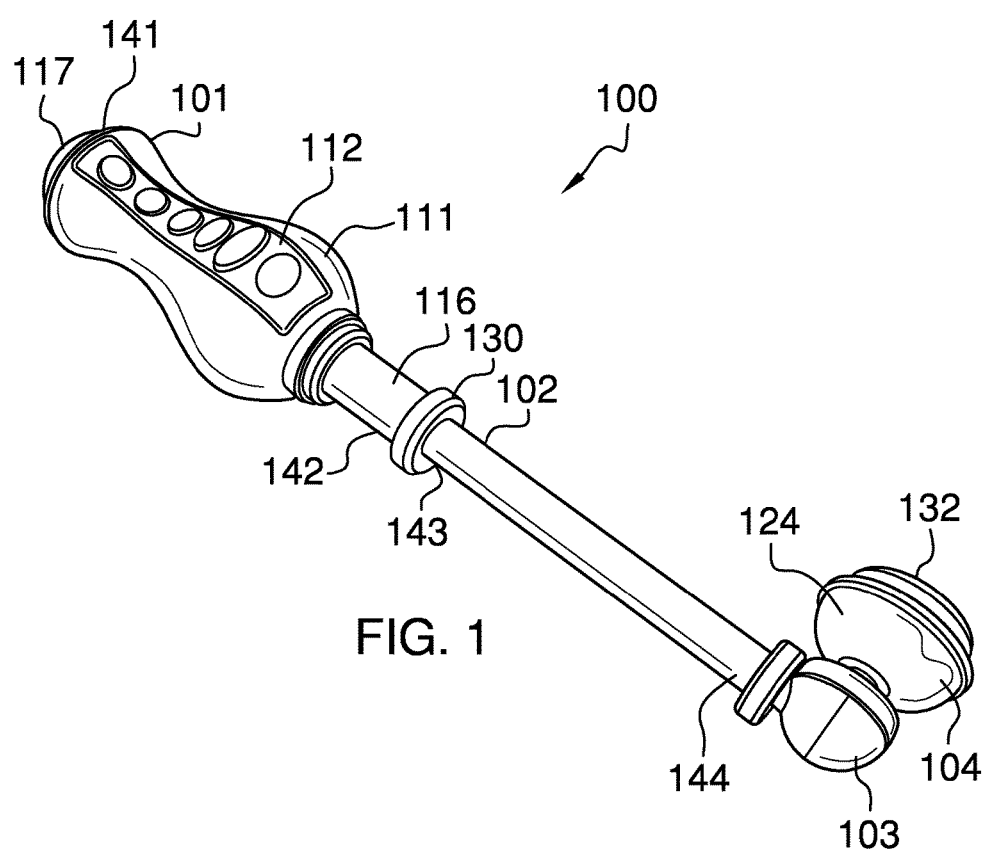
FIG. 1 is a perspective view of an embodiment of the disclosure.
Figure 2:
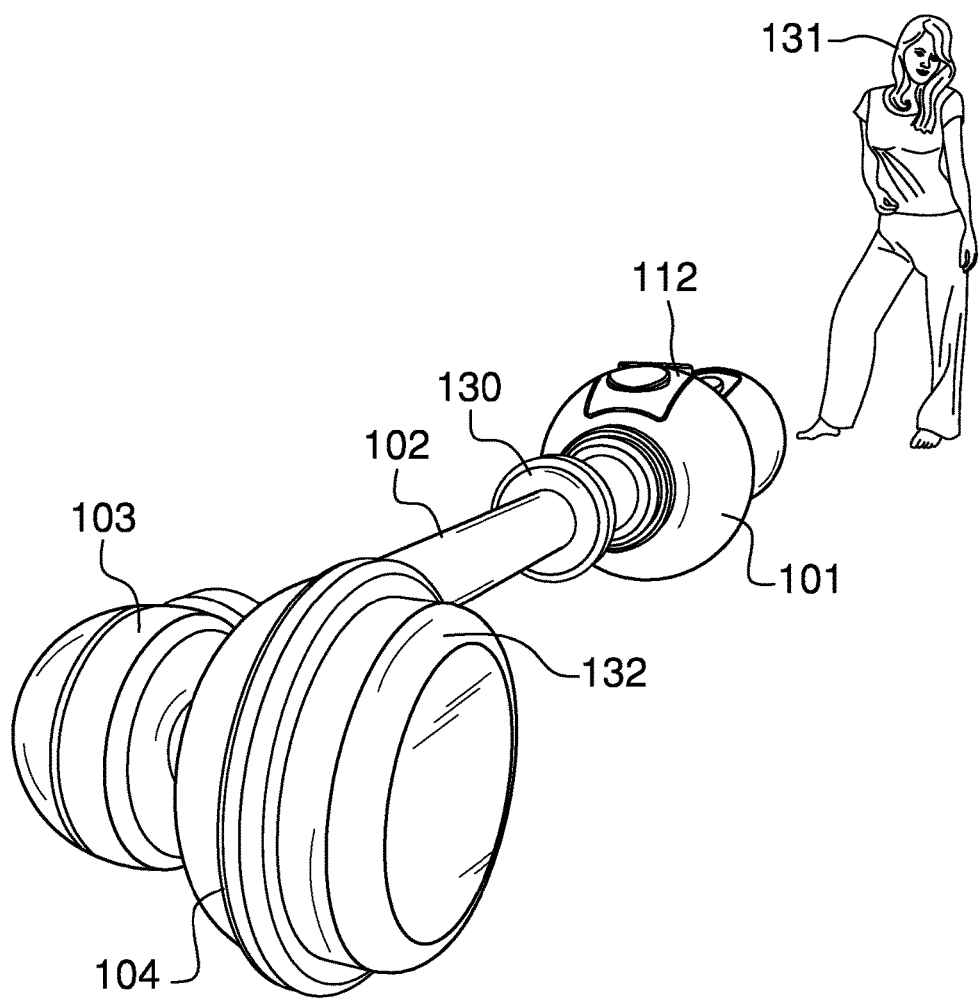
FIG. 2 is an alternate perspective view of an embodiment of the disclosure.
Figure 3:
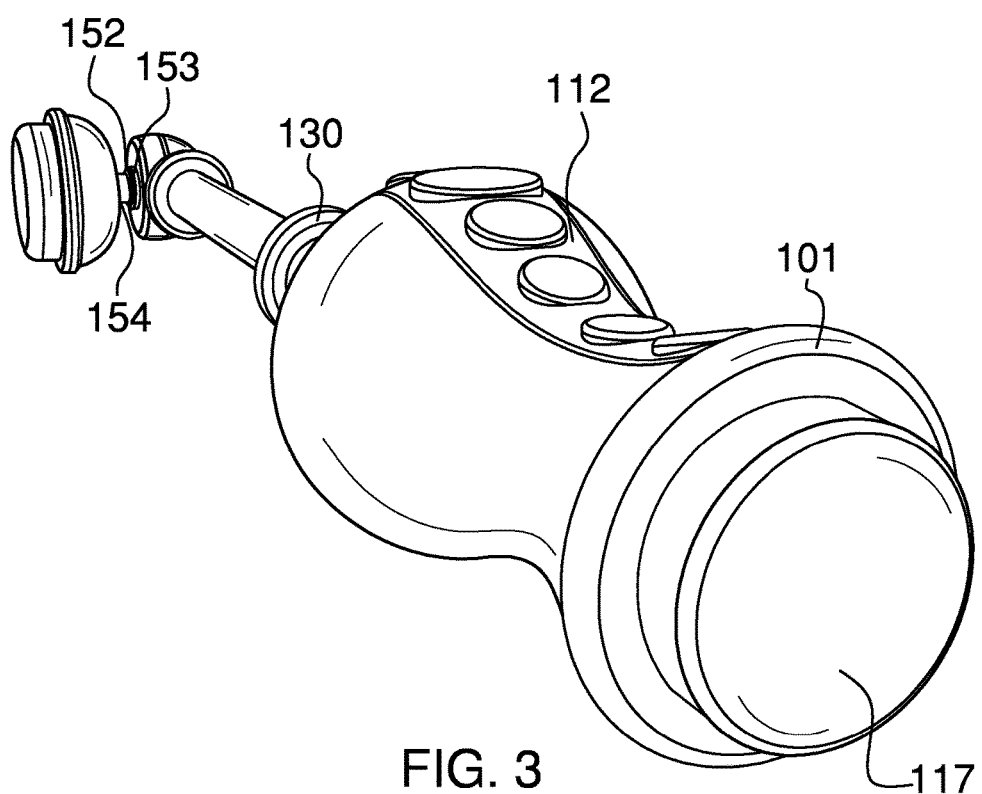
FIG. 3 is an alternate view of an embodiment of the disclosure.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to a first potential embodiment of the disclosure, which is illustrated in FIGS. 1 through 7.

The pedicure device with telescoping pumice stone 100 (hereinafter invention) comprises a handle 101, a telescopic wand 102, a motor cap 103, and a stone cap 104.

The handle 101 is used as a grip through which the user 131 can manipulate and control the invention 100. The handle 101 further comprises a tube 111, a hand grip 112, a master switch 113, a speed control circuit 114, a speed control switch 115, an end tube 116, an end cap 117, and an electrical power source 118. The handle 101 is further defined with a first end 141 and the second end 142. The tube 111 is hollow and provides the main structure of the handle 101. The outer surface of the tube 111 is formed with a variable diameter. The specific pattern of the variable diameter is selected to allow the user 131 to comfortably hold the handle 101. The exterior surface of the tube 111 is at least partially covered with a hand grip 112. The hand grip 112 is an elastic material that further allows the user 131 to comfortably and securely hold the handle 101. The tube 111 and hand grip 112 also have mounted on it the master switch 113, and the speed control switch 115. The purpose of the master switch 113 is to control the flow of electricity to an electric motor 121 that is discussed elsewhere in this disclosure.

The interior of the tube 111 contains the electrical power source 118, the speed control circuit 114, and the motor wiring 129 of the invention 100. The electrical power source 118 is used to provide electricity to the speed control circuit 114 and the electric motor 121. The electrical power source 118 can be a device that draws power off the national electrical grid or can be an internal electrical power source 118 such as a battery 127. In the first potential embodiment of the disclosure, the electrical power source 118 is a battery 127. The purpose of the speed control circuit 114 is to control the rotational speed of the electric motor 121. Techniques for building motor control circuits for this purpose are well known, documented and commercially available in the electrical arts. The electric motor 121 is discussed elsewhere in this disclosure.

Access to the interior of the tube 111 is controlled by the end cap 117. The end cap 117 is a protective lid that is screwed onto the first end 141 of the handle 101 to close off the aperture that provides access to the interior of the tube 111. The end tube 116 is a tube that projects away from the handle 101 from the second end 142 of the handle 101. The end tube 116 is sized to receive a telescopic wand 102 which is discussed elsewhere in this disclosure. Specifically, the end tube 116 provides access into a tube chamber 128 in which the telescopic wand 102 can be stored.

Figure 4:
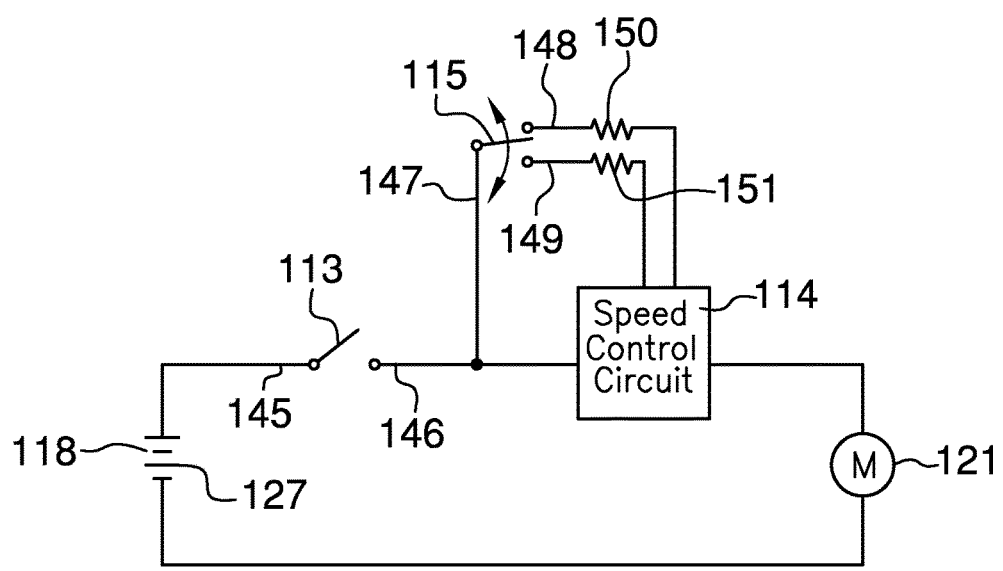
FIG. 4 is a schematic view of an embodiment of the disclosure.
Figure 5:
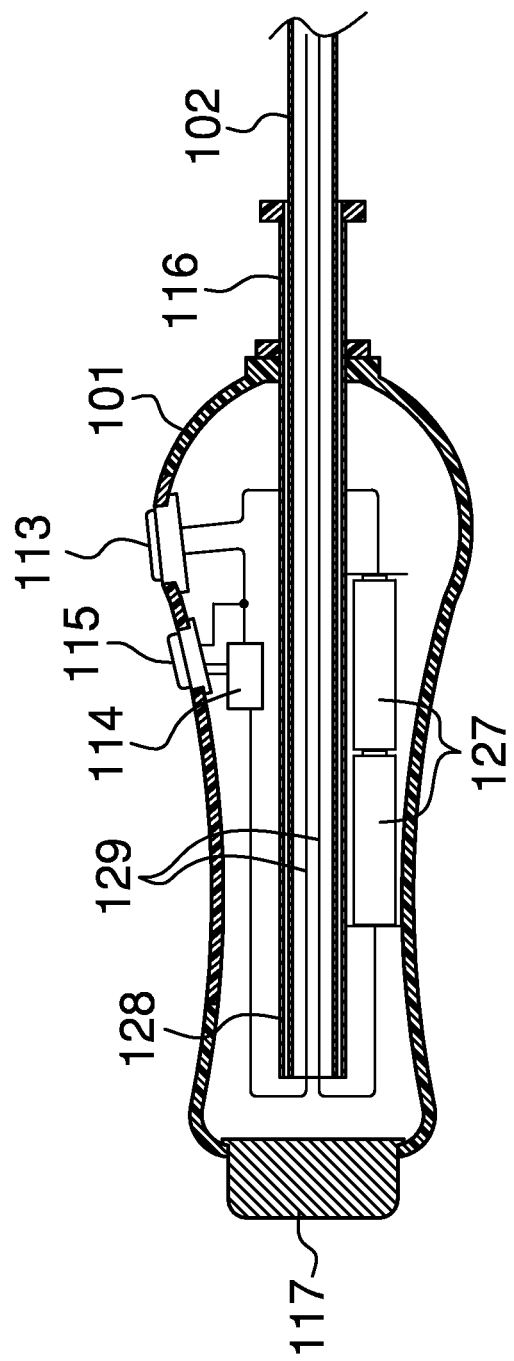
FIG. 5 is a detail view of an embodiment of the disclosure.
Figure 6:
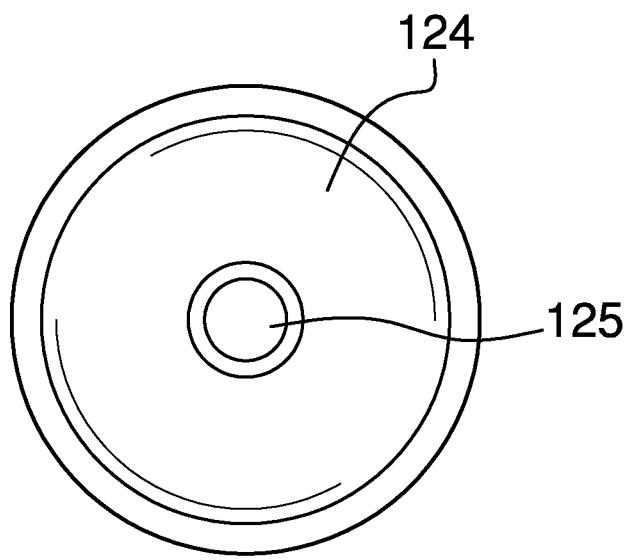
FIG. 6 is a detail view of an embodiment of the disclosure.
Figure 7:
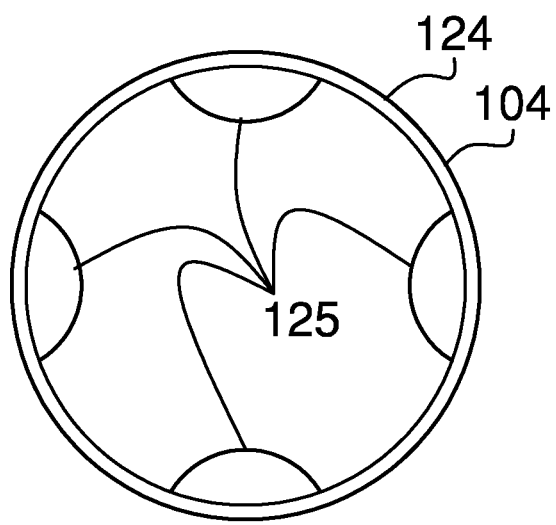
FIG. 7 is a detail view of an embodiment of the disclosure.

As shown in FIG. 4, the electrical power source 118 is wired to a first lead 145 of the master switch 113. A second lead 146 of the master switch 113 is wired to a third lead 147 of the speed control switch 115. The speed control switch 115 is a single pole double throw switch that further comprises a fourth lead 148 and a fifth lead 149. The fourth lead 148 is attached through a first resistor 150 into the speed control circuit 114. The fifth lead 149 is attached through a second resistor 151 into the speed control circuit 114. The speed control circuit 114 adjusts the rotation of the electric motor 121 based whether current is flowing through the first resistor 150 or the second resistor 151. The motor wiring 129 runs through the telescopic wand 102.

The telescopic wand 102 is a hollow tube that is used to connect the motor cap 103 to the handle 101. The telescopic wand 102 is further defined with a third end 143 and a fourth end 144. The third end 143 of the telescopic wand 102 is sized to fit within the end tube 116 located at the second end 142 of the handle 101. The telescopic wand 102 can be variably positioned in the handle 101. By varying the position of the telescopic wand 102 within the handle 101, the overall length of the invention 100 can be adjusted. The telescopic wand 102 is held in position relative to the handle 101 with a telescopic tube lock 130 that is fitted at the end of the end tube 116.

The motor cap 103 is a housing that is attached to the fourth end 144 of the telescopic wand 102. The motor cap 103 contains within it the electric motor 121 that is used to rotate the pumice stone 132. Provisions are made within the motor cap to allow the motor wiring 129 to enter the motor cap 103 and reach the electric motor 121. A first shaft 152 extends away from the electric motor 121 along the axis of rotation of the electric motor 121. The first shaft 152 is used to connect the stone cap 104 to the motor cap 103 and to rotate the pumice stone 132.

The stone cap 104 comprises a shell 124 and a stone grip 125. The shell 124 is a hemispherical rigid surface. The interior of the shell 124 contains the stone grip 125. The stone grip 125 comprises a plurality of springs that are adapted to securely hold the pumice stone 132 in place. The exterior of the shell 124 is fitted with female connector 126 formed at the pole of the hemisphere. The first shaft 152 is further defined with a thirteenth end 153 and a fourteenth end 154. The thirteenth end 153 is attached to the electric motor 121. The fourteenth end 154 is fitted with a key that is designed to match the female connector 126. When the fourteenth end 154 is placed within the female connector 126, the fourteenth end 154 is locked into place.

To use the invention 100, the telescopic wand 102 is placed and locked at its desired length. The master switch 113 is turned on. This powers the speed control circuit 114 and the electric motor 121 which rotates the electric motor 121. The rotation of the electric motor 121 rotates the stone cap 104 which in turn rotates the pumice stone 132. The rotating pumice stone 132 is placed against the foot where it removes dead skin from the heels and bottom of the users 131 feet. To change the speed of rotation of the electric motor 121, the position of the speed control switch 115 is changed.

The following definition was used in this disclosure:

Elastic: As used in this disclosure, an elastic is a material or object that deforms when a force is applied to it and that is able to return to its original shape after the force is removed.

With respect to the above description, it is to be realized that the optimum dimensional relationship for the various components of the invention described above and in FIGS. 1 through 7, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A personal grooming device for use in foot care comprising:
    a handle having a hollow interior with a battery power source and speed control circuit retained in the hollow interior, an outer surface of the handle being formed with a variable diameter, the outer surface being at least partially covered with a hand grip for comfortably holding the handle, a master switch and a speed control switch are mounted on the outer surface, an end cap mounted at a proximal end of the handle, an end tube projecting from an opposing distal end of the handle, where the master switch turns the device on and off and is operatively coupled to the battery power source, the speed control switch and the speed control circuit;
    a telescopic wand extending distally outwardly from the end tube to a terminal distal end;
    a motor cap attached to the terminal distal end of the telescopic wand, the motor cap comprising an electric motor having a first shaft which defines an axis of rotation of the electric motor;
    a stone cap attached to the first shaft of the motor cap, where the stone cap comprises a shell having an interior containing a plurality of springs retaining an abrasive grooming element for abrading skin of a user, where the electric motor rotates the stone cap and the abrasive grooming element about the axis of rotation;
    wherein the telescopic wand is a hollow tube and is variably positioned in the interior of the handle such that an exposed length of the telescopic wand defined as the length of the telescopic wand extending from the end tube is adjusted to vary the overall length of the invention and the telescopic wand is selectively held in a fixed position relative to the handle with a telescopic tube lock and the speed control switch is a single pole double throw switch coupled to the speed control circuit via first and second resistors, where the speed control switch is selectively moved from a non-operative position to one of a first position corresponding to the first resistor and a second position corresponding to the second resistors to allow current to flow through a respective one of the first and second resistors to adjust rotational speed of the electric motor and when the speed control switch is in the non-operative position and the master control switch is turned on, current flows directly through the speed control circuit to rotate the motor.

* * * * *